United States Patent
Carlsson

(10) Patent No.: US 10,022,563 B2
(45) Date of Patent: Jul. 17, 2018

(54) IMAGE-GUIDED RADIOTHERAPY

(71) Applicant: Elekta AB (Publ), Stockholm (SE)

(72) Inventor: Per Carlsson, Stockholm (SE)

(73) Assignee: ELEKTA AB (PUBL), Stockholm (SE)

( * ) Notice: Subject to any disclaimer, the term of this patent is extended or adjusted under 35 U.S.C. 154(b) by 0 days.

(21) Appl. No.: 15/273,293

(22) Filed: Sep. 22, 2016

(65) Prior Publication Data

US 2017/0007850 A1  Jan. 12, 2017

Related U.S. Application Data

(62) Division of application No. 14/266,622, filed on Apr. 30, 2014, now Pat. No. 9,526,917.

(30) Foreign Application Priority Data

Apr. 30, 2013 (GB) .................................. 1307806.8

(51) Int. Cl.
*A61N 5/10* (2006.01)
*A61B 6/03* (2006.01)

(52) U.S. Cl.
CPC ............ *A61N 5/1067* (2013.01); *A61B 6/032* (2013.01); *A61N 5/107* (2013.01); *A61N 5/1049* (2013.01);
(Continued)

(58) Field of Classification Search
CPC .... A61N 5/1045; A61N 5/1067; A61N 5/107; A61N 5/10
See application file for complete search history.

(56) References Cited

U.S. PATENT DOCUMENTS 5,471,516 A * 11/1995 Nunan ................. A61N 5/1049
378/124
6,865,254 B2 * 3/2005 Nafstadius ........... A61N 5/1049
378/4
(Continued)

FOREIGN PATENT DOCUMENTS

| EP | 2 630 989 A1 | 8/2013 |
| GB | 2418336 A | 3/2006 |
| WO | WO 2008/043378 A1 | 4/2008 |

OTHER PUBLICATIONS

Search Report under Search 17(5) in related U.K. Application No. GB1307806.8, dated Oct. 29, 2013, 4 pages.
(Continued)

*Primary Examiner* — Thomas R Artman
(74) *Attorney, Agent, or Firm* — Finnegan, Henderson, Farabow, Garrett & Dunner, L.L.P.

(57) ABSTRACT

A radiotherapy apparatus comprises a rotatable gantry, supporting a source of therapeutic radiation and a source of diagnostic radiation, the two sources being rotationally (or angularly) spaced apart around a rotation axis of the gantry, with at least one collimator associated with the source of therapeutic radiation and arranged to limit the cross-sectional area of a beam produced by that source, a control means arranged to conduct a treatment fraction using the apparatus by causing the apparatus to i. acquire images of a patient using the source of diagnostic radiation, ii. retain those images at least temporarily, iii. subsequently, after further rotation of the gantry, select a retained image acquired when the source of diagnostic radiation was at a rotational position corresponding to the instantaneous rotational position of the source of therapeutic radiation, and iv. control the beam relative to the patient using information derived from the selected image. The corresponding rota-
(Continued)

tional position is ideally one in which the source of therapeutic radiation is at the same or substantially the same rotational position as was the source of diagnostic radiation at the point in time when the image was acquired. An alternative a radiotherapy apparatus comprises a rotatable gantry supporting a source of therapeutic radiation and a source of diagnostic radiation, at least one collimator associated with the source of therapeutic radiation and arranged to limit the cross-sectional area of a beam produced by that source, a reconstruction means arranged to i. obtain two-dimensional images of a patient using the source of diagnostic radiation, ii. retain those images at least temporarily, iii. apply a recency threshold to the retained images thereby to exclude images less recent than the threshold, iv. select at least three such retained images meeting the recency threshold and reconstruct a CT volume or tomographic image using the selected images, and a control means arranged to conduct a treatment fraction or treatment session using the apparatus, controlling the collimator using information derived from the CT volume.

10 Claims, 2 Drawing Sheets

(52) U.S. Cl.
CPC .... *A61N 5/1081* (2013.01); *A61N 2005/1061* (2013.01)

(56) References Cited

U.S. PATENT DOCUMENTS

| | | | |
|---|---|---|---|
| 7,227,925 B1 | 6/2007 | Mansfield et al. | |
| 8,306,189 B2* | 11/2012 | Brown | H01J 35/00 378/125 |
| 8,355,482 B2* | 1/2013 | Brown | A61N 5/1049 378/124 |
| 8,848,999 B2* | 9/2014 | Boese | A61B 6/4007 382/131 |
| 8,917,813 B2* | 12/2014 | Maurer, Jr. | A61N 5/10 378/197 |
| 2004/0005027 A1* | 1/2004 | Nafstadius | A61N 5/1049 378/65 |
| 2007/0025509 A1 | 2/2007 | Pang et al. | |
| 2011/0080990 A1 | 4/2011 | Filiberti et al. | |
| 2011/0210261 A1* | 9/2011 | Maurer, Jr. | A61N 5/10 250/393 |
| 2011/0268341 A1* | 11/2011 | Boese | A61B 6/4007 382/132 |
| 2012/0051515 A1 | 3/2012 | Brown | |

OTHER PUBLICATIONS

Search Report under Section 17(6) in related U.K. Application No. GB1307806.8, dated Apr. 17, 2014, 2 pages.

* cited by examiner

IMAGE-GUIDED RADIOTHERAPY

CROSS REFERENCE TO RELATED APPLICATIONS

This is a division of application Ser. No. 14/266,622, filed Apr. 30, 2014, which claims the benefit of priority to GB 1307806.8, filed Apr. 30, 2013, both of which are expressly incorporated herein by reference in their entirety.

FIELD OF THE INVENTION

The present invention relates to image-guided radiotherapy.

BACKGROUND ART

Radiotherapy is the process of treating a tumour or other lesion (hereinafter referred to as a "tumour") by directing a beam of harmful radiation, usually ionising radiation, such as an x-ray or electron beam, towards the lesion. The beam can be produced by an electron gun such as a linear accelerator, which produces a beam of high-energy electrons (typically in the 2-5 MeV range) which may be directed toward the patient or toward an x-ray target in order to produce an x-ray beam. A flattening filter can be inserted into the beam in order to produce a more even illumination across the cross-section of the beam.

Clearly, the beam has the potential to cause harm to the normal healthy tissue around the lesion, as well as to the tumour itself. It is therefore normal to collimate the beam so that the dose delivered to healthy tissue is minimised whereas the dose delivered to the tumour is maximised—or at least optimised, as there may be a need to limit the overall dose delivered in any one session in order to avoid necrosis and other potential complications. The direction from which the beam is delivered to the tumour can also be varied by placing the source on a gantry that is rotatable around the patient, so that different volumes of healthy tissue are in front of or behind the tumour at any one time, and this the time for which the additional dose is delivered to any particular region of healthy tissue is minimised.

Many types of collimator are available, in particular the "multi-leaf collimator" which comprises a large number (typically 40, 80 or 160) of leaves, each of which is long and thin but relatively deep in the beam direction. These are disposed adjacent each other with their long edges projecting into the beam from one side, and can be moved independently of each other into and out of the beam field. The tips of the leaves thus define an edge whose shape can be varied at will by moving individual leaves into or out of the beam.

There are various approaches to using the above arrangements to deliver a beam. Rotational conformal therapy, for example, involves rotating the radiation source around the tumour during the treatment while adjusting the multi-leaf collimator so that the cross-sectional shape of the beam matches the projected shape of the tumour along the instantaneous direction of the beam. Intensity modulated radiation therapy uses mathematical methods which start from a segmented volume identifying regions that are within the tumour (together with a desired dose), regions that are outside the lesion, and regions into which dose must be minimised, and a definition of the apparatus capabilities, and derives a treatment plan involving rotation of the gantry, collimator shapes, and dose rates which delivers a three-dimensional dose distribution which satisfies the various constraints.

All delivery methods share a common need to know the current shape and location of the lesion. However, this changes with time and between treatments. As the tumour reduces in volume in response to the treatment, it may move and allow other organs that it had displaced to return towards their usual positions. Generally, organs in the abdomen are also apt to move over time in any case, especially those below the diaphragm. At the simplest level, the patient may move during the treatment, or may be placed on the apparatus in a slightly different position or pose.

Typically, radiotherapy is delivered in a series of individual doses on a regular (e.g. daily) basis—usually referred to as "treatment fractions" or just "fractions". To account for changes in the tumour position or shape between fractions, i.e. "inter-fraction motion", a diagnostic image is taken immediately prior to treatment and the current position and/or shape of the tumour is determined. This is then used to adjust the treatment plan as necessary. The diagnostic image may be one or more x-ray images, or a computed tomography ("CT") scan. Such diagnostic imaging needs a lower energy x-ray source in order to provide high quality images, typically in the range of up to 125 keV, rather than the high-energy (5 MeV) beam used for treatment which can be used for imaging, but provides very poor contrast between human tissue types. Often, a low-energy diagnostic source is provided on the same gantry in combination with the therapeutic source in order to allow for this. As the gantry is rotatable around the patient in order to allow for irradiation from multiple directions, this rotation can be used to allow the diagnostic source to develop a cone-beam CT ("CBCT") reconstruction. Usually, the diagnostic source is located on the gantry 90 degrees from the therapeutic source, so that with the associated imaging panels for each source opposite the respective source, the items on the gantry are spaced apart and access is maximised.

It is possible to use the therapeutic beam to obtain images of the patient during treatment, a so-called "portal image". However, as noted the image quality is poor due to a marked lack of contrast. Generally, this is adequate to confirm the gross positioning of the patent only.

To control for movement of the patient during a fraction, i.e. "intra-fraction motion management" ("IFMM"), it is more usual to attempt to fix the patient in position. The patient can be placed in an individually-tailored shaped cushion in order to ensure consistent positioning on the patient table and to limit movement during a treatment fraction, as for example disclosed in our application WO2009/006925. Restraints may be provided in order to limit movement of the patient and/or urge internal organs into a consistent position, such as is for example shown in our application WO2008/040379. For radiotherapy of the head region, a frame may be attached directly to the skull and used to fixate the head in a reproducible position. Moulded face masks can also be used to place the patient's head in a reproducible position; this is less accurate than a frame but much less invasive.

Some efforts are made to detect and respond to changes in the patient position, such as reflective markers attached to the exterior of the patient which can be detected visually. However, these are an indirect measure of the tumour position and hence of lower accuracy.

U.S. Pat. No. 7,227,925 discloses a radiation therapy treatment machine that has a stereoscopic imaging system, which includes a rotatable open gantry on which is placed a therapeutic radiation source between two diagnostic radiation sources, each with an associated diagnostic imager. The images from the two diagnostic sources are combined to produce a stereoscopic image that has location and depth information, which is used to guide the therapeutic source. In order to create a good stereoscopic image, there needs to be two diagnostic sources, placed one either side of the therapeutic source, ideally symmetrically.

SUMMARY OF THE INVENTION

In its first aspect, the present invention therefore provides a radiotherapy apparatus, comprising a rotatable gantry, supporting a source of therapeutic radiation and a source of diagnostic radiation, the two sources being rotationally (or angularly) spaced apart around a rotation axis of the gantry, with at least one collimator associated with the source of therapeutic radiation and arranged to limit the cross-sectional area of a beam produced by that source, a control means arranged to conduct a treatment fraction using the apparatus by causing the apparatus to i. acquire images of a patient using the source of diagnostic radiation, ii. retain those images at least temporarily, iii. subsequently, after further rotation of the gantry, select a retained image acquired when the source of diagnostic radiation was at a rotational position corresponding to the instantaneous rotational position of the source of therapeutic radiation, and iv. control the beam relative to the patient (such as by adjusting the collimator or moving a patient support) using information derived from the selected image.

The corresponding rotational position is ideally one in which the source of therapeutic radiation is at the same or substantially the same rotational position as was the source of diagnostic radiation at the point in time when the image was acquired.

In a second aspect, the invention provides a radiotherapy apparatus, comprising a rotatable gantry supporting a source of therapeutic radiation and a source of diagnostic radiation, at least one collimator associated with the source of therapeutic radiation and arranged to limit the cross-sectional area of a beam produced by that source, a reconstruction means arranged to i. obtain two-dimensional images of a patient using the source of diagnostic radiation, ii. retain those images at least temporarily, iii. apply a recency threshold to the retained images thereby to exclude images less recent than the threshold, iv. select at least three such retained images meeting the recency threshold and reconstruct a CT volume using the selected images, and a control means arranged to conduct a treatment fraction or treatment session using the apparatus, controlling the collimator using information derived from the CT volume.

The recency threshold can be applied by deleting images beyond the threshold, discarding them, or otherwise ignoring them. One example of a suitable threshold is a maximum value for the time that has elapsed since the image was acquired. Another is a maximum value for the angle through which the gantry has rotated since the image was acquired. A further example of a suitable threshold is one that is met by an image if the image is one of the most recent n images where n is a preset integer.

The source of therapeutic radiation and the source of diagnostic radiation can be provided in the same head. Ideally, the source of therapeutic radiation and source of diagnostic radiation are provided by the same linear accelerator, obtained by applying different settings thereto. Our previous applications WO1999/040759, WO2001/011929 and WO2001/011928 (all of which are hereby incorporated by reference) show how this can be done.

Alternatively, the source of therapeutic radiation and source of diagnostic radiation can be provided in separate heads. The resulting two sources are then preferably spaced radially apart around a rotation axis of the gantry—ideally by an acute angle, preferably less than 45 degrees.

The source of therapeutic radiation typically emits a beam of radiation with an energy of at least 1 MeV. Likewise, the source of diagnostic radiation typically emits a beam of radiation with an energy of at least 50 keV, typically up to 150 keV.

The collimator is preferably a multi-leaf collimator, but can be of any sort apt to limit the cross-section of the therapeutic beam.

BRIEF DESCRIPTION OF THE DRAWINGS

An embodiment of the present invention will now be described by way of example, with reference to the accompanying figures in which.

DETAILED DESCRIPTION OF THE EMBODIMENTS

To ensure that the patient is positioned correctly prior to treatment, and to note any inter-fraction changes in the tumour position & shape and/or patient anatomy, a cone-beam CT image ("CBCT") is usually taken before treatment starts, and the patient positioning is adjusted so that the dose can reach the desired target. Sometimes, one or more intermediate CBCTs are done during the treatment fraction, during which the treatment is stopped and after which the patient repositioned to increase the treatment accuracy.

The inherent problem is that perfect fixation of the patient during treatment is difficult. With a frame attached to the skull, patient movements are typically very small, such as less than 0.5 mm. However, with other fixation techniques such as a facial mask there tend to be significantly greater patient movements. For extracranial treatments, there are greater difficulties in fixation of the target, with corresponding results. Meanwhile, the accuracy of delivery is important, in that a lesser accuracy demands a greater margin of treatment volume around the tumour (the so-called "planning target volume" or PTV; in order to ensure that the entire tumour is treated, which thus increases the dose delivered to healthy tissue and may place nearby sensitive structures at risk.

The embodiments of the present invention are especially suited to overcoming slow to medium IFMM, such as in intracranial, scull, soft tissue, spine, cervical spine and prostate treatments where the target is normally quite still during treatment and that a non-periodic spontaneous movement may occur at any time, or a slower drift of the target location at rates normally ranging up to several seconds per mm (although individual movements faster than this could occur). It is however the total dose to the PTV that must be controlled, so even spontaneous fast movements can be tolerated as long as they are very few and are compensated for within a few seconds after they have occurred so that the total dose error is well within limits. There are two operating methods that are provided by the invention, a first that is applicable to the embodiment illustrated in FIG. 1, and a second that is applicable to both the embodiment of FIG. 1 and the embodiment of FIG. 2.

Figure 1:
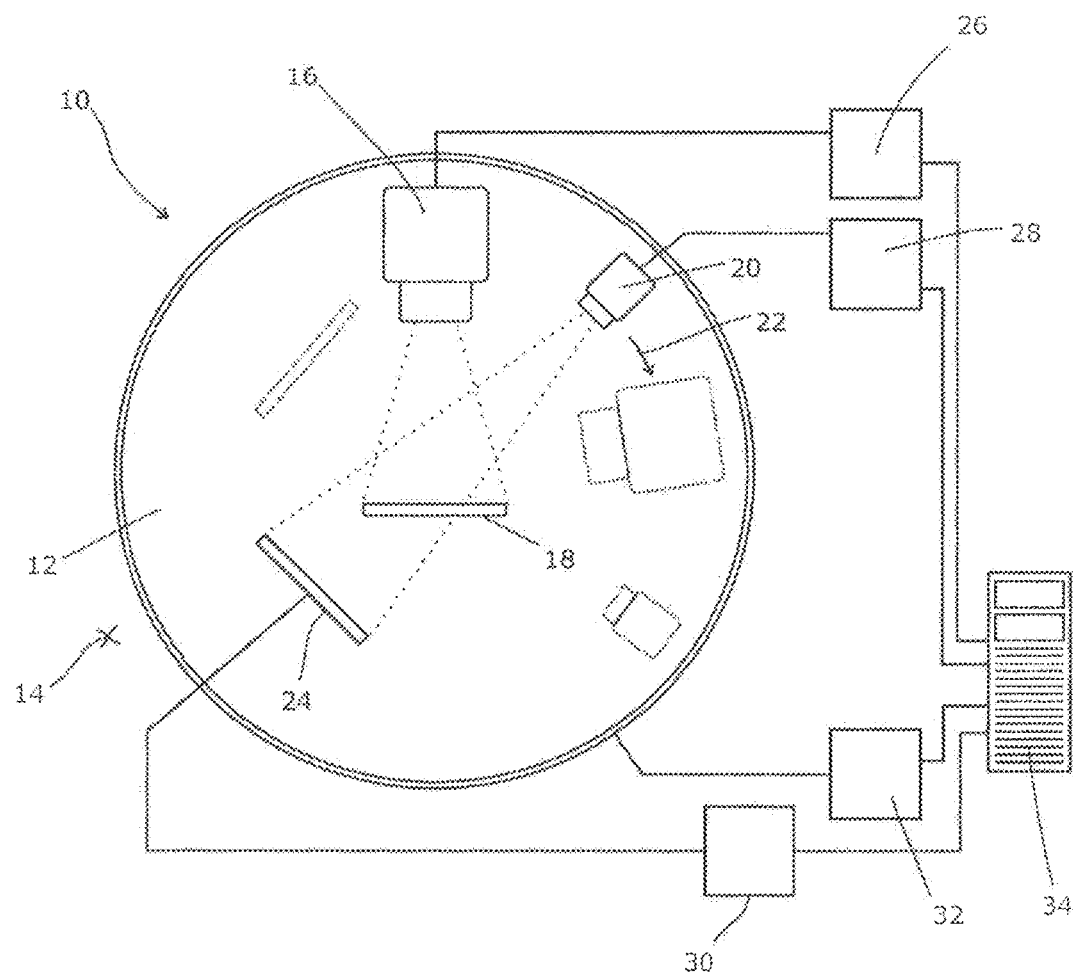
FIG. 1 shows the arrangement of a radiotherapy apparatus according to a first embodiment.
Figure 2:
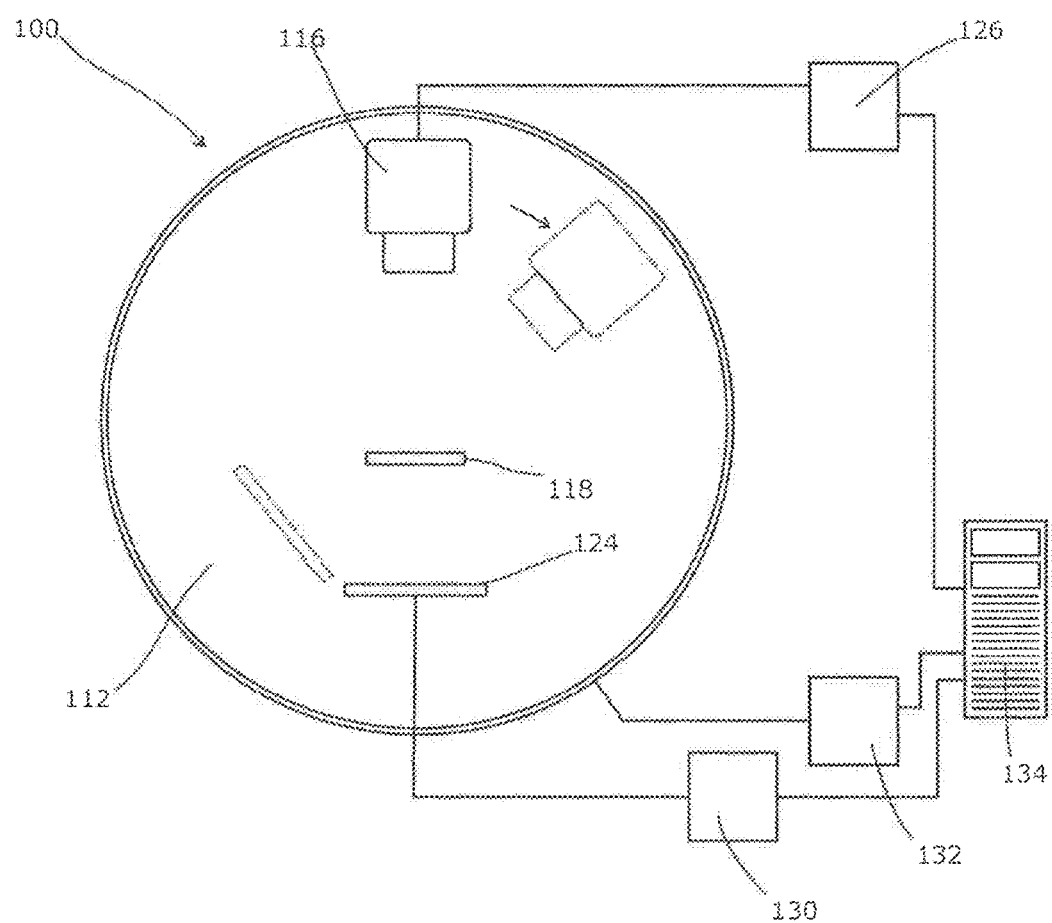
FIG. 2 shows the arrangement of a radiotherapy apparatus according to a second embodiment.

Referring to FIG. 1 which shows the first embodiment, a radiotherapy apparatus 10 comprises a support 12 which is rotatable about a central horizontal axis. Usually, the bulk of the support 12 is concealed behind a wall or false wall or covers 14 through which the support projects. A gantry projects from the support 12 and carries a therapeutic head 16 which produces a high-energy beam suitable for therapeutic purposes, directed toward the central horizontal axis. To create the beam, a linear accelerator is located within the support 12 and the gantry, ending in the therapeutic head 16. A relativistic beam of electrons from the accelerator is directed onto an x-ray target to produce a beam of high-energy x-rays in the appropriate direction. This is then filtered if necessary, such as with a flattening filter, and collimated by block collimators and multi-leaf collimators to create a therapeutically useful beam.

A patient table 18 is provided, just below the central horizontal axis, to position a patient with the target or tumour site at the point of intersection of the central horizontal axis and the central axis of the therapeutic beam—a point typically referred to as the "isocentre". The patient table 18, shown schematically in FIG. 1, is usually driven by suitable motors an as to allow adjustment in all six degrees of freedom (three translational and three rotational) in order to position the patient precisely relative to the isocentre. The treatment room is usually provided with low-power laser markers which converge on the isocentre from a variety of directions such as the three orthogonal directions in order to assist with this process.

A diagnostic head 20 is supported on a second gantry, located a few degrees away from the therapeutic head 16, for example 10-45 degrees. This emits a low-energy diagnostic beam of up to about 125 keV in energy towards the isocentre, suitable for producing high-contrast images of human tissue. FIG. 1 shows the diagnostic head 20 at the preferred upper bound of 45° from the therapeutic head 16. The two heads should be arranged on the support relative to the rotation direction 22 such that the diagnostic head 20 is before the therapeutic head 16 when rotating. A flat-panel imager 24 is also provided on the support 12, directly opposite the diagnostic head 20 in order to obtain a two-dimensional x-ray image of the patient. A second flat-panel imager may also be provided opposite the therapeutic head 16, but this is not shown.

Control units are provided for the two radiation heads 16, 20 and for the flat panel imager 24. These comprise a therapeutic head controller 26 which controls the therapeutic beam and the collimators, a diagnostic head controller 28 which controls and triggers the diagnostic beam, an imager controller 30 which triggers the flat-panel imager 24 and reads the image together with the gantry angle and pairs them together, and a gantry controller 32 which directs the motors in the support 12 to rotate the support 12 and gantries as necessary. All four controllers report to a central control and processing computer 34. Of course, the control functions may be arranged differently, such as by further subdividing different functions and/or by amalgamating functions.

According to the first operating method, the apparatus delivers a treatment fraction, alternating between emitting one or more pulses of the therapeutic beam and emitted a pulse or pulses of the diagnostic beam (and capturing the corresponding images), while rotating the support 12 around a patient on the patient table 18. Each 2D image is stored by the computer 34 together with the rotation angle at which it was obtained, derived from the gantry controller 32. The images are analysed by the computer 34 to detect positioning error and adjust the collimator settings that will be needed when the therapeutic beam is emitted from that rotation angle. Then, when the support has rotated by a further angle corresponding to the angular difference between the two heads 16, 20, the adjusted collimator settings are passed to the therapeutic head controller 26.

In other words, as the support rotates during a treatment, a continuous series of diagnostic images are obtained which are inspected for movement, and the therapeutic beam is controlled based on an image (previously) obtained from the diagnostic system when it was at the gantry angle currently occupied by the therapeutic beam. When the therapeutic beam is at the same angle as the diagnostic, the 2D information contains all information necessary to exactly hit the target—where that target is visible in the 2D image (such as via bony anatomy, markers and the like). Although the target may be displaced from its previous position in a direction along the beam axis, such movements will only affect the dose to target very marginally and within acceptable limits.

For an angular speed of (for example) 30 degrees per second, the treatment error (or lag) will be about one second, and it will be possible to track the target with a lag of one second behind. For spine or intracranial treatments with a facial fixation mask this is acceptable and would result in a very small dosimetric error. The main factor that is controllable is of course the chosen angle between the two heads, with a smaller angle leading to a more recent image being used and hence a smaller error. In practice, though, the lower bound of the angle is likely to be limited by space constraints and (possibly) by the minimum processing time needed for each image.

According to the second operating method, instead of guiding the therapeutic beam using a single recent 2D image, it is guided according to a CBCT image made up from a rolling selection of recent 2D images. Thus, during the treatment the apparatus is controlled so as to take images continuously, timed between pulses of the therapeutic beam for minimum interference. A CBCT stack of images is maintained, to which new images are added and images older than a defined threshold are deleted. Alternatively, all or substantially all of the images may be retained and a selection filter applied to choose those images meeting a recency criterion for use by the CT reconstruction algorithm. Thereby, a continuous volumetric image is created that follows movements of the patient anatomy as an average over the relevant recent period. The algorithm could also be improved so that newer images are more weighted regarding positioning determination.

A preferred recency criterion for the images is simply to retain (or choose) the images obtained during the last 180 degrees of gantry movement. This has the advantage of allowing a good quality reconstruction as all points of view are included. At a rotation rate of (say) 30°/s, this corresponds to six seconds, so is responsive to patient movement. Other angular values could however be chosen, such as 90 degrees, or different recency criteria could be used. For example, a set time limit could be used, with images "expiring" after a set time of (say) 5 seconds. Alternatively, a set number of images could be retained, effectively creating a simple FIFO buffer for the images with each new image causing the deletion or expiry of the oldest image left in the buffer. An advantage of using volumetric images is that the visibility of and ability to track soft tissue movements is increased.

The second operating method could be put into effect using the apparatus described with reference to FIG. 1. Alternatively, it could use the apparatus of the second embodiment shown in FIG. 2. This radiotherapy apparatus 100 comprises a support 112, rotatable about a central horizontal axis, generally the same as the support 12 of FIG. 1. A single head 116 produces either a high-energy beam suitable for therapeutic purposes, or (selectably) a low-energy diagnostic beam of up to about 125 keV in energy, suitable for producing high-contrast images of human tissue. Both beams are emitted along the same axis, directed towards the isocentre.

A linear accelerator is located within the support 112 and the gantry, ending in the head 116. An adjustable-energy relativistic beam of electrons from the accelerator is directed onto an x-ray target to produce a beam of high-energy x-rays in the appropriate direction. This is then filtered if necessary, such as by a flattening filter, and collimated by block collimators and multi-leaf collimators to create a therapeutically useful beam. The output energy of the x-ray beam can be controlled by adjusting the energy of the electron beam, as explained in our earlier applications WO1999/040759, WO2001/011929 and WO2001/011928 (all of which are hereby incorporated by reference).

A patient table 118 is also provided, corresponding to the table 18 of FIG. 1.

A flat-panel imager 124 is also provided on the support 112, directly opposite the single head 116 in order to obtain a two-dimensional x-ray image of the patient. This can be controlled by an imager controller 130 to capture just diagnostic images, or both diagnostic and portal images.

Control units are provided for the radiation head 116 and for the flat panel imager 121. These comprise a radiation head controller 126 which controls the therapeutic beam, the diagnostic beam and the collimators, an imager controller 130 (as mentioned) which triggers the flat-panel imager 124 and reads the image, and a gantry controller 132 which directs the motors in the support 112 to rotate the support 112 and gantries as necessary. All four controllers report to a central control and processing computer 131. Of course, the control functions may be arranged differently, such as by further subdividing different functions and/or by amalgamating functions.

It will of course be understood that many variations may be made to the above-described embodiment without departing from the scope of the present invention. Equally, the technique is applicable to designs of radiotherapy apparatus other than those disclosed herein. Such alternative forms may include different forms of radiation such as electron or proton beams, or other forms of collimation, or other forms of delivery such as those employing a second angle of the treatment head for (e.g.) non-co-planar treatment geometries.

The invention claimed is:

1. A radiotherapy apparatus, comprising:
   a rotatable gantry, supporting a source of radiation, wherein the source of radiation is selectably configurable to produce a beam that is either a high-energy beam or a low-energy beam;
   at least one collimator associated with the source of radiation, and configured to limit a cross-sectional area of the beam produced by the source of radiation;
   a reconstruction device configured to:
     obtain images of a patient using the low-energy beam of the source of radiation;
     retain the obtained images at least temporarily;
     apply a threshold to the retained images to exclude images obtained before the threshold; and
     select at least three retained images meeting the threshold and reconstruct a CT volume using the selected images, wherein a first image of the selected images is weighted more heavily than a second image of the selected images when reconstructing the CT volume, the first image having been obtained after the second image; and
   a control device configured to conduct a treatment fraction using the high-energy beam of the source of radiation, and control the at least one collimator using information derived from the CT volume.

2. The radiotherapy apparatus according to claim 1, wherein the threshold is applied by deleting images obtained before the threshold.

3. The radiotherapy apparatus according to claim 1, wherein the threshold is met by an image if the image was acquired after a preset time.

4. The radiotherapy apparatus according to claim 1, wherein the threshold is met by an image if the rotatable gantry has rotated by less than a preset angle since the image was acquired.

5. The radiotherapy apparatus according to claim 1, wherein the threshold is met by an image if the image is one of the most recent N images where N is a preset number.

6. The radiotherapy apparatus according to claim 1, wherein the high-energy beam includes therapeutic radiation, the low-energy beam includes diagnostic radiation, and the high-energy beam and the low-energy beam are provided by a same linear accelerator.

7. The radiotherapy apparatus according to claim 1, wherein the source of radiation is provided by a linear accelerator.

8. The radiotherapy apparatus according to claim 1, wherein the high-energy beam has an energy of at least 1 MeV.

9. The radiotherapy apparatus according to claim 1, wherein the low-energy beam has an energy of less than 150 keV.

10. The radiotherapy apparatus according to claim 1, wherein the collimator is a multi-leaf collimator.

* * * * *